United States Patent
Minarikova

(10) Patent No.: US 6,989,085 B2
(45) Date of Patent: Jan. 24, 2006

(54) METHOD FOR SEPARATION OF COMPOUNDS USING CYCLING DENATURING CONDITIONS

(75) Inventor: Lucie Minarikova, Prague (CZ)

(73) Assignee: Genomac International, Ltd., Prague (CZ)

(*) Notice: Subject to any disclaimer, the term of this patent is extended or adjusted under 35 U.S.C. 154(b) by 63 days.

(21) Appl. No.: 10/723,892

(22) Filed: Nov. 26, 2003

(65) Prior Publication Data

US 2004/0118685 A1 Jun. 24, 2004

Related U.S. Application Data

(60) Provisional application No. 60/430,169, filed on Dec. 2, 2002.

(51) Int. Cl.
C07K 1/26 (2006.01)
G01N 27/26 (2006.01)

(52) U.S. Cl. .................. 204/452; 204/453; 204/603; 204/604

(58) Field of Classification Search ............... 204/164, 204/450–453, 600–603
See application file for complete search history.

(56) References Cited

U.S. PATENT DOCUMENTS

| 5,633,129 A | 5/1997 | Karger et al. ............... 435/6 |
| 6,156,178 A | 12/2000 | Mansfield et al. .......... 204/457 |
| 6,174,675 B1 * | 1/2001 | Chow et al. ................ 435/6 |

OTHER PUBLICATIONS

Q. Li et al., "Integrated Platform for Detection of DNA Sequence Variants using Capillary Array Electrophophoresis", Electrophoresis 2002, 23, 1499-1511.

J. Schell et al., "Detection of Point Mutations by Capillary Electrophoresis with Temporal Temperature Gradients", Electrophoresis 1999, 20, 2864-2869.

* cited by examiner

Primary Examiner—Kaj K. Olsen
Assistant Examiner—R. Michelle Vestal
(74) Attorney, Agent, or Firm—Schneck & Schneck; Thomas Schneck; David M. Schneck

(57) ABSTRACT

A method for electrophoretic separation in separation channels in which the temperature of the channel is repeatedly cycled during the course of the separation.

12 Claims, 5 Drawing Sheets

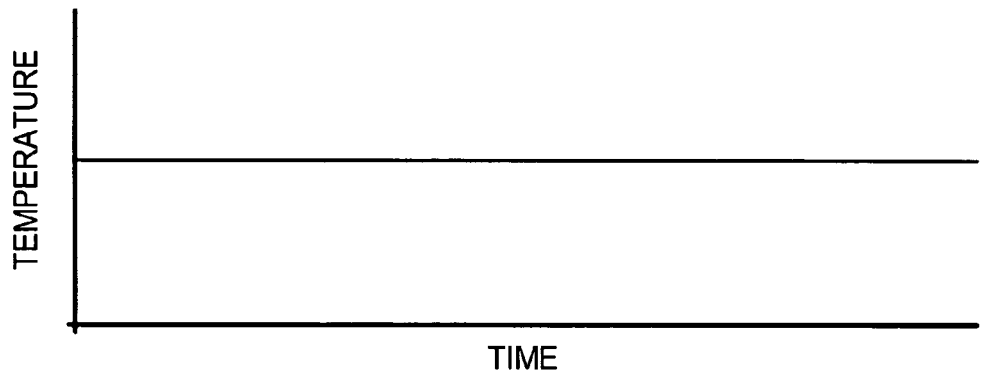
Fig._1A
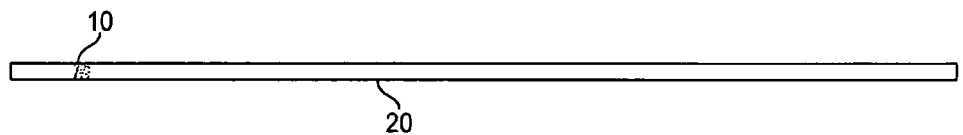
Fig._1B

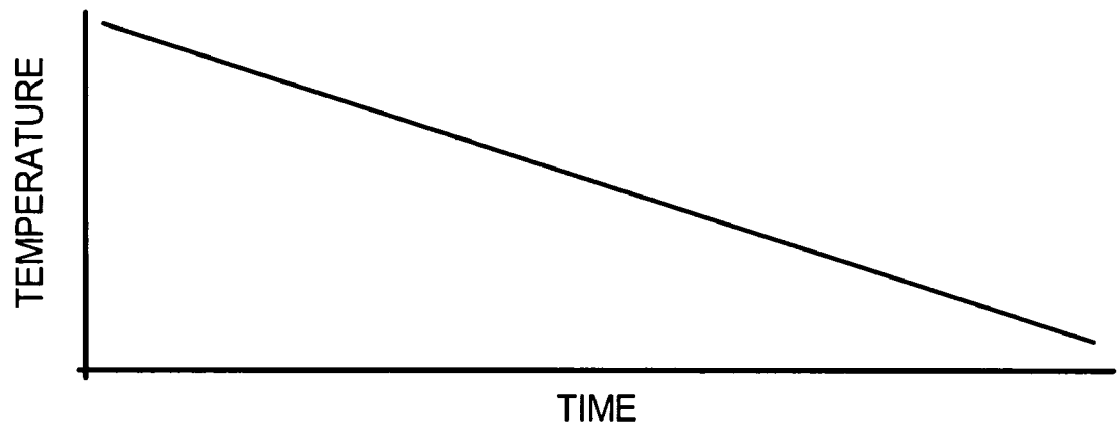
Fig._2A
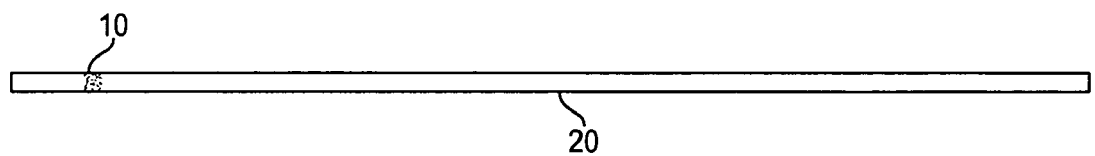
Fig._2B

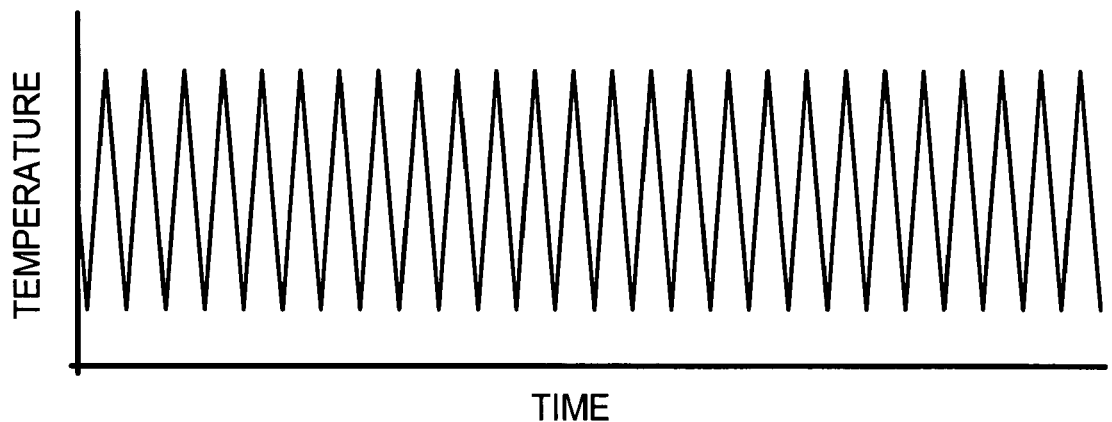
*Fig._3A*
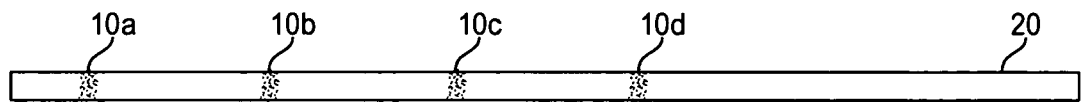
*Fig._3B*

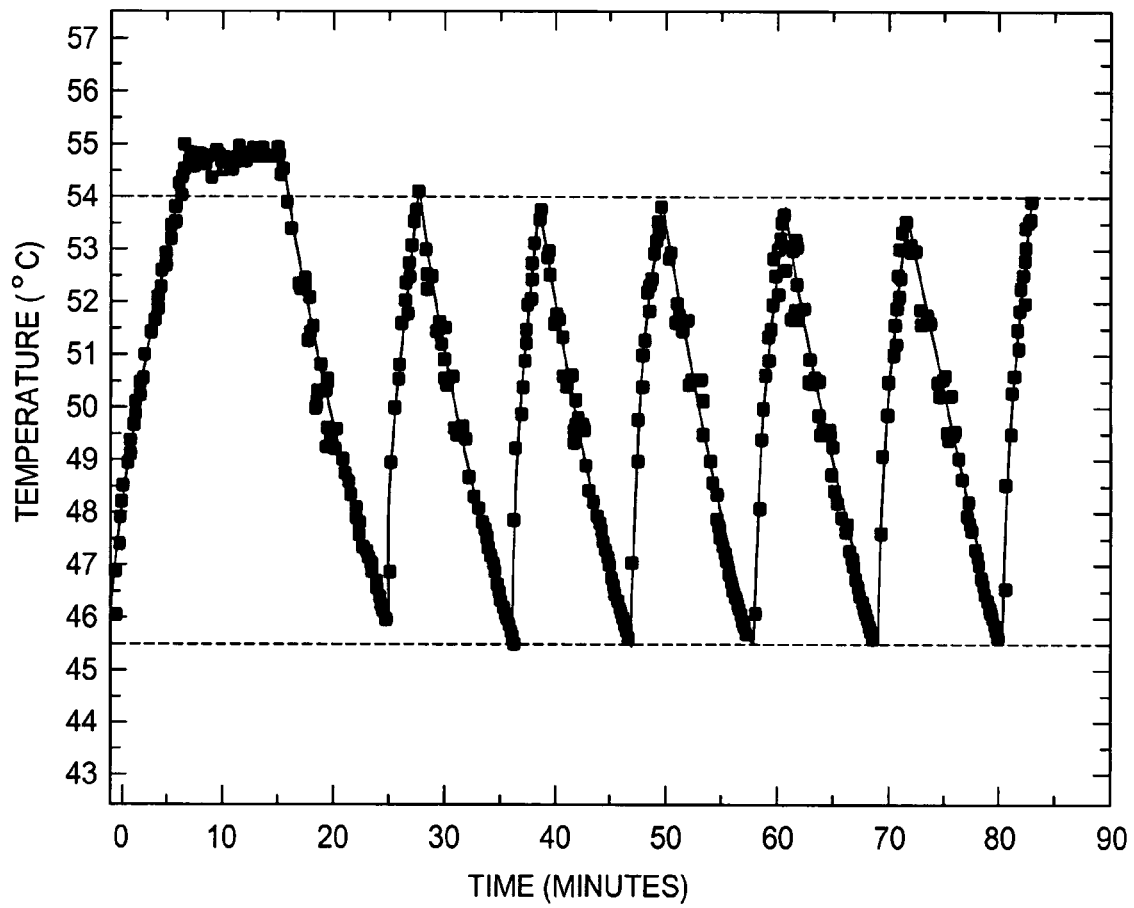
Fig. _4

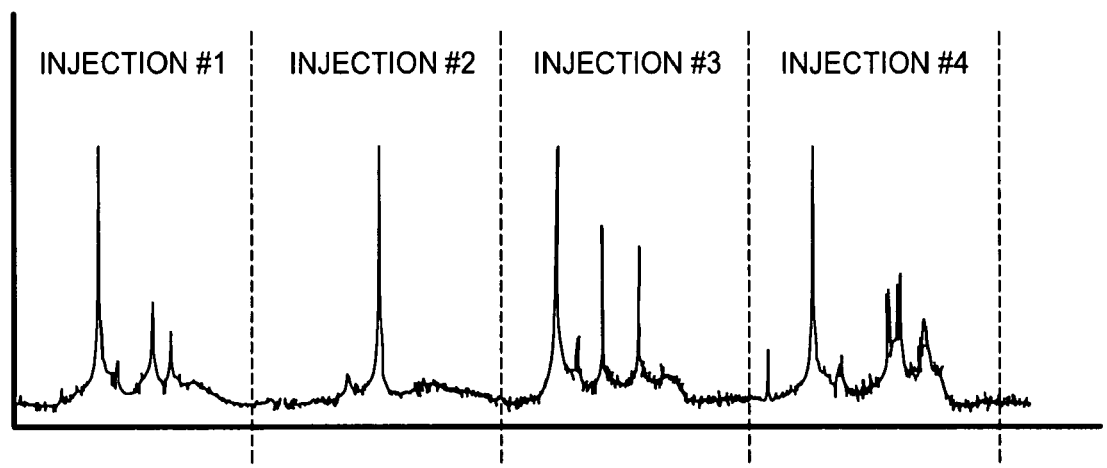
Fig._5

METHOD FOR SEPARATION OF COMPOUNDS USING CYCLING DENATURING CONDITIONS

CROSS REFERENCE TO RELATED APPLICATION

This application claims priority from U.S. provisional application No. 60/430,169, filed Dec. 2, 2002.

TECHNICAL FIELD

The present invention relates generally to separation and analysis of compounds and more specifically to means of separating compounds based on their secondary structure under partial or fully denaturing conditions.

BACKGROUND OF THE INVENTION

Analysis of DNA variations (mutations or polymorphisms) is central to many applications in genetics, genomics as well as in clinical research and diagnostics. One commonly used approach is based on separation of PCR amplified fragment of a target sequence under partial denaturing conditions. The partial denaturation is usually achieved by a chemical denaturant or raising the temperature.

Maintaining an accurate optimum temperature at which mutants in the studied target sequence possesses different conformation from the non-mutated (wildtype) sequence over the duration of electrophoretic or chromatographic separation is generally difficult. A more common approach is to use a temperature gradient during which sooner or later the separated fragments reach their optimum temperature, provided that the temperature range of such gradient is sufficiently wide (Schell et at. 1999). Applying temperature gradients became recently popular in multicapillary electrophoresis systems (Li et al. 2002). With temperature gradients, the reproducibility among different capillaries in an array is better compared to constant temperature control approach. However one problem still remains. The period of time during which the fragment is subjected to its melting optimum depends of the gradient slope i.e. rate at which the temperature is changed. Prior to analysis of an unknown sample it is essential to optimize the temperature settings with respect to the temperature range and gradient slope. Also in some multi-channel systems, it is difficult to control a single-sweep temperature gradient profile reproducibly in all channels at once. As a result the resolution as well as channel-to-channel reproducibility is often not optimal. Finally the overall sample throughput of a single-sweep gradient system is limited due to the relatively long time duration required for the gradient to be completed over the entire course of the separation.

It is an object of this invention to provide a method for separation of compounds (such as DNA molecules) under partially or fully denaturing conditions.

It is a further object of the invention to provide a method not requiring complex optimization of separation parameters such as the denaturant gradient slope.

It is a further object of the invention to provide a method applicable to detection of DNA mutations and polymorphisms using multiple-injection technology for increased sample throughput.

It is a further object of the invention to provide a method applicable to multi-channel separation instruments without a need of complex changes in instrumentation design.

SUMMARY OF THE INVENTION

The above objects have been achieved through application of multiple cycles of temperature gradient during the course of separation. During each of the cycles the temperature is changed from a starting temperature point to the ending temperature point, at some point reaching partial or complete melting temperature (Tm) of each of the individual components within the sample mixture. Melting in this context means separation of double stranded DNA into single strands. The periodical exposition of the components to their melting temperatures aids in their separation by means of electrophoresis, chromatography or other processes applied in the system. The revolving optimum separation conditions allow for application of multiple-injection technology where different sample mixtures may be periodically injected in phase with the repeating cycles. The separation can be performed in a single column (e.g. single capillary tube) or a micro-fabricated channel (e.g. channels in a substrate or chip) or in an array of columns or micro-fabricated channels. The main area of applicability is in high-throughput discovery, detection and screening of genetic variations (DNA mutations and polymorphisms).

BRIEF DESCRIPTION OF THE DRAWINGS

FIG. 1A is a graph of temperature over time in constant temperature separations.

FIG. 1B is a schematic of a capillary tube during a single injection, constant temperature separation.

FIG. 2A is a graph of a single-sweep temperature gradient.

FIG. 2B is a schematic of a capillary tube during a single injection during a typical temperature-gradient capillary electrophoresis (TGCE).

FIG. 3A is a graph of temperature over time by applying a series of temperature cycles.

FIG. 3B is a schematic of a capillary tube during a multiple-injection experiment.

FIG. 4 is a graph of the temperature profile inside MEGABACE 1000® capillary array instrument during a cycling temperature gradient experiment.

FIG. 5 shows a readout of optically detected signals during analysis of a multiple-injection separation of DNA mutants using cycling temperature gradient conditions.

DETAILED DESCRIPTION OF THE INVENTION

In the described method a new approach to separation of compounds from mixtures based their partial or complete denaturation is presented. In one embodiment it utilizes a series of temperature gradient cycles to achieve revolving optimum conditions to separate individual compounds from a sample mixture. The periodical application of the optimum temperature conditions aids separation in which multiple samples are injected in the course of a single experiment by means for multiple-injection technology, such as U.S. Pat. No. 6,156,178 hereby expressly incorporated by reference herein.

With reference to FIG. 1B, during a classical capillary electrophoretic separation a sample 10 is injected onto a separation channel 20 (e.g. capillary) and separated at a constant temperature. The applied separation temperature needs to be previously determined to be optimum for ideal resolution of compounds within the sample mixture (as in U.S. Pat. No. 5,633,129 to Karger et al. hereby incorporated by reference herein). Maintaining accurate constant temperature is relatively difficult especially in multichannel systems, where a plurality of samples are injected and separated in parallel. There the overall heat dissipation usually results in a higher temperature in channels closer to the array center and lower temperature in the (better cooled) channels on its sides. Even relatively small differences (<0.5 C) might result in significant changes in separation patterns if the same sample is analyzed in different channels. Temperature over time is graphically illustrated in FIG. 1A.

One partial solution of the non-uniform temperature distribution problem is by application of a single-sweep temporal temperature gradient. With this approach each channel undergoes a range of changing conditions, but the overall impact of the partial denaturation in all channels is roughly equilibrated. Yet, with single-sweep temperature gradient (as shown in graph 2A) it is still necessary to carefully optimize the temperature gradient slope to match the duration of sample migration for each of the sample compounds to be analyzed. As in FIG. 1B, FIG. 2B indicates a single sample 10 is separated in capillary 20.

FIG. 3A shows a graph illustrating the proposed improvement of the single-sweep temperature gradient technique by applying a series of temperature cycles. With such cycling temperature gradients, there is no need for matching the gradient slope to the duration of the electrophoretic migration since during each cycle, channels are repeatedly subjected to optimum separation temperatures. In addition to the overall/simplification of the technique; the use of periodical cycling gradient further enables a significant increase in sample throughput by application of multiple-injection technique as illustrated in FIG. 3B. In FIG. 3B samples 10a–10d are injected into capillary 20 at intervals. In a multiple-injection experiment, samples are serially injected onto a separation channel (or an array of channels) in periodical time intervals (see Mansfield et al. U.S. Pat. No. 6,156,178). The main advantage of this approach is increase in a number of samples analyzed per experiment. Applying multiple injection method is not possible with single-sweep temperature gradients, since the samples eluting at the early stage of the experiment would be subjected to different temperature range compared to the ones injected later. With the temperature gradient cycling each of the serially injected samples undergoes similar number of cycles before reaching the detector, thus is subjected to equivalent separation conditions. As illustrated in FIG. 3A, the cycles are uniform temperature cycles. However, either or both of the temperature range or duration of the cycles may be altered. It is still preferred that in the interval between subsequent injections the temperature cycles be identical (e.g. if the pattern is one long and two short cycles from high to low temperature, this pattern be repeated between each sample injection.

FIG. 4 shows a temperature profile recorded during a cycling temperature gradient experiment using MEGABACE 1000® capillary array instrument. The cycling gradient range was set from 54° C. to 46° C. with a cycling frequency of 1 cycle per 10 minutes.

FIG. 5 shows a practical example of application of cycling temperature gradient approach. Four different DNA samples (k-ras exon 1 PCR amplicons from colorectal tumor samples) were serially injected onto a single capillary and analyzed using cycling gradient conditions with cycling temperature range from 52° C. to 50° C. and cycle rate of 2 minutes per cycle.

Those of skill in the art would recognize that the disclosed temperature cycling during electrophoresis could be used on single capillary systems, capillary array systems, or capillary (microchannel) chips. Any of a number of available systems could be used for electrophoretically separating and detecting samples. Detectors include fluorescence detectors, mass spectrometry detectors and others. If a commercially available system is used, the system can be instructed to automatically cycle between a high and low temperature. If multiple samples are injected, a sample is injected followed by a separation interval, followed by a second injection, followed by a second separation interval. This process is repeated until all samples are loaded into the capillary. All of the samples are then continuously detected. It is preferred that during the time between injections the sample be cycled between high and low temperature settings at least 2 times.

What is claimed is:

1. A method for capillary separation of a sample comprising:
   injecting the sample into a separation channel;
   electrophoretically separating the sample in the separation channel;
   exposing the separation channel to a cycling temperature gradient while electrophoretically separating the sample; and
   detecting separated compounds in said sample.

2. The method of claim 1, wherein said separation channel is a capillary tube.

3. The method of claim 1, further comprising repeating all steps of claim 1 in a plurality of capillaries in a capillary array.

4. The method of claim 1, wherein said separation channel is on a micro-fabricated substrate.

5. The method of claim 4, wherein said micro-fabricated substrate includes a plurality of separation channels and steps of claim 1 are repeated in each channel.

6. A method for separating compounds comprising:
   a) injecting a sample into a separation channel;
   b) migrating the sample for a specified interval;
   c) repeating steps a and b a plurality of times;
   d) following a final sample injection, continuously detecting separated samples; and
   e) exposing the separation channel to a cycling temperature gradient during steps a, b, c, and d such that a plurality of temperature cycles occur between each sample injection.

7. The method of claim 6, wherein said separation channel is a capillary tube.

8. The method of claim 6, further comprising repeating all steps of claim 6 in a plurality of capillaries in a capillary array.

9. The method of claim 6, wherein said separation channel is on a micro-fabricated substrate.

10. The method of claim 9, wherein said micro-fabricated substrate includes a plurality of separation channels and steps of claim 1 are repeated in each channel.

11. The method of claim 6, wherein the cycling temperature gradient has identical duration and temperature range cycles.

12. The method of claim 6, wherein the cycling temperature gradient has variable duration or temperature range cycles.

* * * * *